(12) United States Patent
Liska et al.

(10) Patent No.: US 9,796,138 B2
(45) Date of Patent: Oct. 24, 2017

(54) DEVICE AND METHOD FOR PROCESSING LIGHT-POLYMERIZABLE MATERIAL FOR BUILDING UP AN OBJECT IN LAYERS

(71) Applicants: Ivoclar Vivadent AG, Schaan (LI); Technische Universitat Wien, Vienna (AT)

(72) Inventors: Robert Liska, Schleinbach (AT); Johannes Patzer, Vienna (AT); Jurgen Stampfl, Vienna (AT); Wolfgang Wachter, Schaan (LI); Christoph Appert, Vaduz (LI)

(73) Assignees: Ivoclar Vivadent AG, Schaan (LI); Technische Universitat Wien, Vienna (AT)

( * ) Notice: Subject to any disclaimer, the term of this patent is extended or adjusted under 35 U.S.C. 154(b) by 0 days.

(21) Appl. No.: 14/255,056

(22) Filed: Apr. 17, 2014

(65) Prior Publication Data
US 2014/0227382 A1    Aug. 14, 2014

Related U.S. Application Data

(62) Division of application No. 13/124,660, filed as application No. PCT/EP2008/008866 on Oct. 20, 2008, now Pat. No. 8,741,203.

(51) Int. Cl.
*B29C 67/00* (2017.01)
*B33Y 30/00* (2015.01)
(Continued)

(52) U.S. Cl.
CPC ...... *B29C 67/0066* (2013.01); *A61C 13/0013* (2013.01); *B33Y 10/00* (2014.12); *B33Y 30/00* (2014.12)

(58) Field of Classification Search
CPC .................................................. B29C 67/0066
See application file for complete search history.

(56) References Cited

U.S. PATENT DOCUMENTS

| 4,752,498 A | 6/1988 | Fudim |
| 5,026,146 A | 6/1991 | Hug et al. |
(Continued)

FOREIGN PATENT DOCUMENTS

| DE | 19953000 A1 | 5/2001 |
| DE | 19957370 A1 | 6/2001 |
(Continued)

OTHER PUBLICATIONS

Jörg Wleklik, Mounting and calibration of the camera on Perfactory machine, 12 pgs., dated Jun. 5, 2012.†

*Primary Examiner* — Larry Thrower
(74) *Attorney, Agent, or Firm* — Ann M. Knab; Thad McMurray

(57) ABSTRACT

A method and a device for processing a light-polymerizable material (5, 55) for building up an object (27) in layers, using a lithography based generative manufacture having a construction platform (12) for building up the object (27), a projecting exposure unit (10, 60) that can be controlled for locally selected exposing of a surface on the construction platform (12, 62) to an intensity pattern having a prescribed shape, and a control unit (11, 61) prepared for polymerizing overlapping layers (28) on the construction platform (12, 62) in successive exposure steps, each having a prescribed geometry, by controlling the projecting exposure unit (10, 60), in order to thus successively build up the object (27) in the desired shape, said shape resulting from the sequence of layer geometries. The invention is characterized in that a further exposure unit (16, 66) for exposing the surface of the construction platform (12, 62) is provided on the side opposite the projecting exposure unit (10, 60), and that the (Continued)

construction platform (12, 62) is designed to be at least partially transparent to light, and that the control unit (11, 61) is designed for controlling the further exposure unit (16, 66) at least while building up the first layer (28), said layer adhering to the construction platform (12, 62), for exposing in the prescribed geometry.

18 Claims, 6 Drawing Sheets

(51) Int. Cl.
    *B33Y 10/00*     (2015.01)
    *A61C 13/00*     (2006.01)

(56) References Cited

U.S. PATENT DOCUMENTS

| | | |
|---|---|---|
| 5,496,682 A | 3/1996 | Quadir et al. |
| 5,876,550 A | 3/1999 | Feygin et al. |
| 7,706,910 B2 * | 4/2010 | Hull et al. .................... 700/120 |
| 7,783,371 B2 † | 8/2010 | John |

FOREIGN PATENT DOCUMENTS

| | | |
|---|---|---|
| DE | 10256672 A1 | 6/2004 |
| DE | 102007006478 A1 | 8/2008 |
| WO | 9600422 A1 † | 1/1996 |
| WO | WO 96/00422 * | 1/1996 |
| WO | 9806560 A1 | 2/1998 |
| WO | 0100390 A1 † | 1/2001 |

\* cited by examiner
† cited by third party

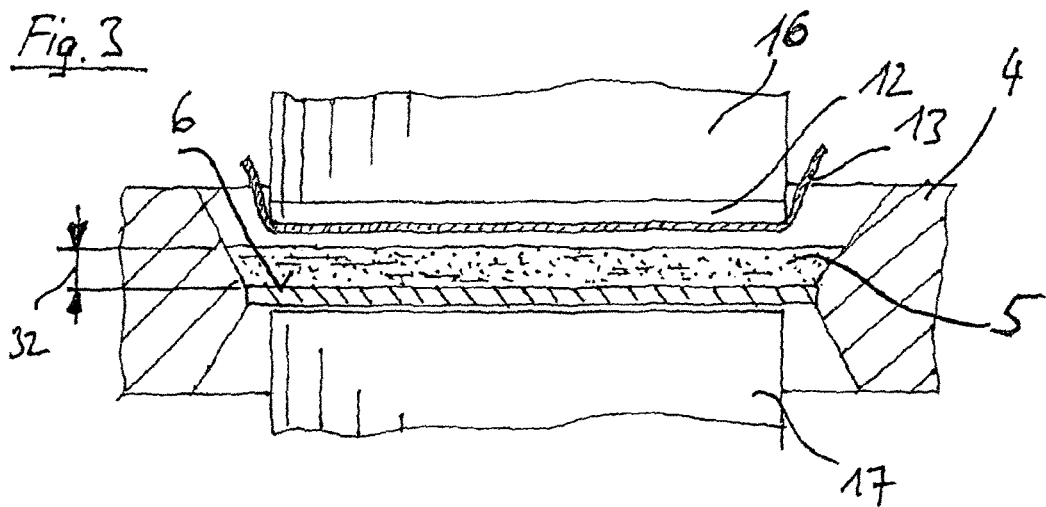
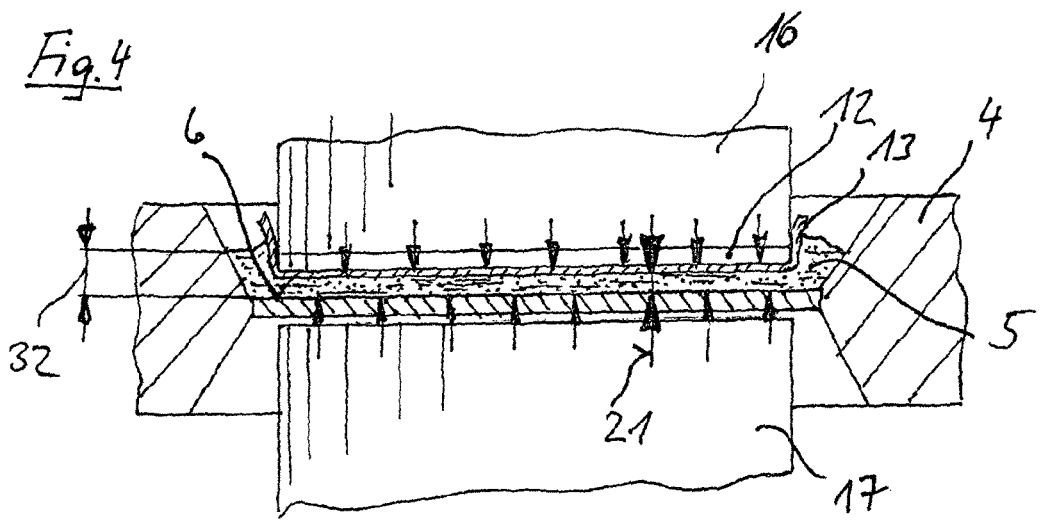
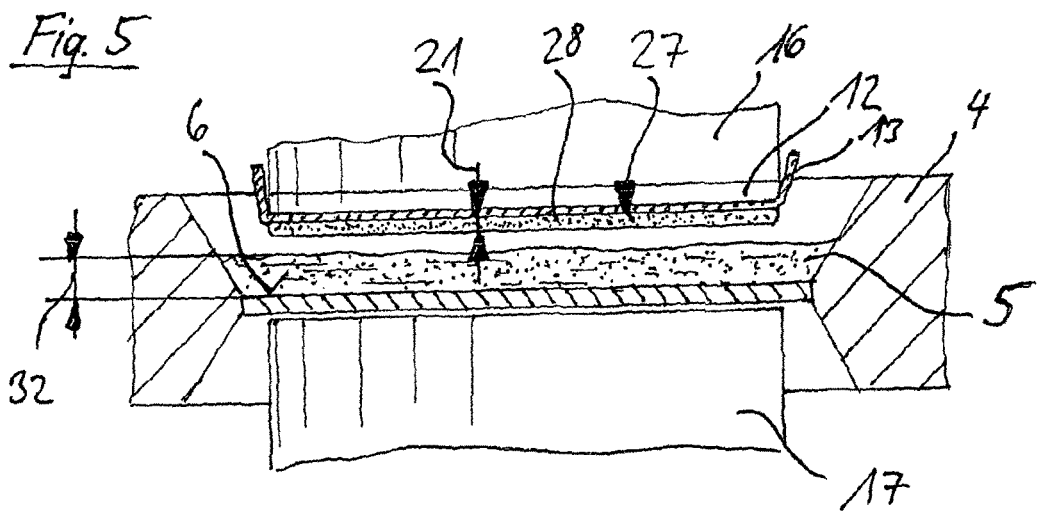

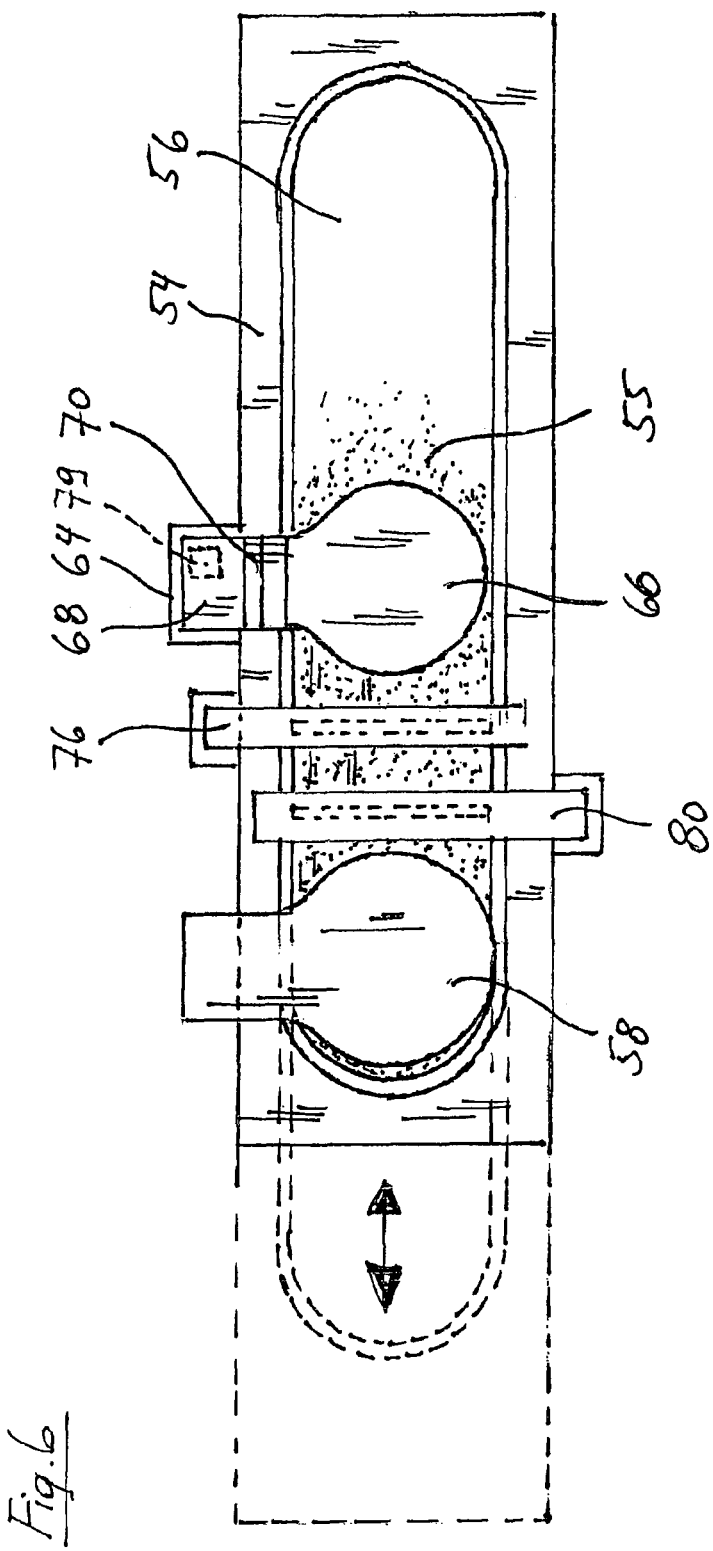

DEVICE AND METHOD FOR PROCESSING LIGHT-POLYMERIZABLE MATERIAL FOR BUILDING UP AN OBJECT IN LAYERS

CROSS-REFERENCE TO RELATED APPLICATIONS

This application is a divisional application of U.S. application Ser. No. 13/124,660, filed Sep. 6, 2011, which of claims the benefit of International Application PCT/EP2008/008866, (International Publication No. WO 2010/045951 A1), filed Oct. 20, 2008, which is hereby incorporated by reference in its entirety.

TECHNICAL FIELD

The invention is directed at the building up of objects and, in particular, to the building up of objects that are intended to be used for dental restorations.

BACKGROUND OF INVENTION

CAD-CAM technologies have been established in the dental sector for some time and have taken the place of the traditional manual crafting of tooth replacements. However, the methods customary today for producing ceramic dental restoration elements by removing material have several disadvantages, which cannot be improved with reasonable expenditure from economic aspects by the current state of the art. In this connection, building-up methods of production that are known under the term "rapid prototyping" can be considered, in particular stereolithographic methods in which a newly applied layer of material is respectively polymerized in the desired form by position selective exposure, whereby the desired body is gradually produced by shaping in layers in its three-dimensional form, which results from the succession of the layers applied.

With respect to ceramic-filled polymers, WO 98/06560, which is hereby incorporated by reference, should be mentioned in particular. In this case, a ceramic slip is exposed by way of a dynamic mask (light modulator), whereby a three-dimensional body is intended to be gradually built up. In the case of the method described, the ceramic slip is exposed from above on a build platform. In the case of such exposure from above, after each exposure a new thin layer of material must be applied with the aid of a doctor blade (typically with a layer thickness which lies between 10 and 100 μm). When using materials of relatively high viscosity, as ceramic-filled resins are, it is only with difficulty, however, that such thin layers can be applied in a reproducible manner.

In the prior art, there are also known techniques, at least for photomonomers without ceramic filling, in which the exposure takes place from below through the bottom of a vat, which is formed by a transparent film, sheet or sheet with an elastomeric surface (for example of silicone or fluoroelastomer). Above the transparent film or sheet there is a build platform, which is held at a settable height above the film or sheet by a lifting mechanism. In the first exposure step, the photopolymer between the film and the build platform is polymerized in the desired form by exposure. When the build platform is raised, the polymerized first layer becomes detached from the film or sheet and liquid monomer flows into the space created. The object polymerized in layers is created by successive raising of the build platform and selective exposure of the monomer material that has flowed in. A device suitable for applying this method is described for example in DE 199 57 370 A1, which is hereby incorporated by reference. A similar procedure is described in DE 102 56 672 A1, which is hereby incorporated by reference, which however likewise relates to unfilled polymers.

In the processing of ceramic-filled photopolymers, the following problems arise in comparison with the processing of unfilled photopolymers:

The green strength of the polymerized objects is significantly lower (less than 10 MPa) than the strength of an unfilled polymer (typically about 20 to 60 MPa). As a result, the ceramic-filled photopolymer object can withstand significantly less mechanical loading (for example when the last-formed layer is detached from the sheet or film through which exposure was performed from below).

The high proportion of ceramic particles causes pronounced light diffusion, and the depth of penetration of the light that is used is significantly reduced. Associated with this is non-uniform polymerization in the z direction (direction of radiation) in the case of layer thicknesses of more than 20 μm. The small depth of penetration also makes it difficult to achieve reliable bonding of the first layer directly on the build platform. In the case of ceramic-filled monomer material, however, it cannot be ensured that the initial starting layer is sufficiently thin (for example less than 75 μm). Consequently, a reproducible bonding force on the build platform could not be ensured even with very long exposure of the first layer.

In comparison with unfilled photopolymers, ceramic-filled polymerizable materials are significantly more viscous. This imposes increased requirements on the exposure mechanism that is used. In particular, the time that is required for ceramic-filled photopolymer to flow in after raising of the build platform may be considerably longer. The raising and lowering of the build platform in a highly viscous photopolymer material also imposes increased requirements to avoid detrimental effects on the component.

On account of the high basic viscosity, ceramic-filled photopolymers are more sensitive to gelling by diffused light or ambient light. Even small light intensities are sufficient to raise the viscosity of the material above the permissible limit by the polymerization taking place.

SUMMARY OF THE INVENTION

The problem addressed by the present invention is that of improving a building method and a device for processing light-polymerizable materials for building up objects, using lithographic rapid prototyping, in such a way that they allow even light-polymerizable materials of relatively high viscosity, in particular ceramic-filled photopolymers, to be processed better.

The device and method according to the independent patent claims serve for solving this problem. Advantageous embodiments of the invention are specified in the subclaims.

The invention relates to a device for processing light-polymerizable material for building up an object in layers, using lithography-based generative fabrication, for example rapid prototyping, with a build platform for building up the object, a projecting exposure unit, which can be controlled for position selective exposure of a surface on the build platform with an intensity pattern with prescribed geometry, and a control unit, which is prepared for polymerizing in successive exposure steps layers lying one above the other on the build platform, respectively with prescribed geometry, by controlling the exposure unit, in order in this way to build up the object successively in the desired form, which results from the sequence of the layer geometries.

The invention also relates to a method for processing light-polymerizable material for building up an object in layers, using a lithography-based generative fabrication technique (rapid prototyping), in which light-polymerizable material is polymerized on a build platform in a layer with prescribed geometry by exposure in an exposure area, the build platform is displaced for the forming of a subsequent layer, light-polymerizable material is newly fed onto the layer last formed, and, by repeating the previous steps, the object is built up in layers in the desired form, which results from the sequence of the layer geometries.

BRIEF DESCRIPTION OF THE FIGURES

Further advantages, details and features emerge from the following description of embodiments of the invention on the basis of the drawings, in which:

FIGS. 3 to 5 show a partial view of the device from FIG. 1 in the region of the build platform and the vat bottom in successive working steps, FIG. 6 shows a plan view from above of a second embodiment of the invention.

DETAILED DESCRIPTION OF THE INVENTION

Figure 1:
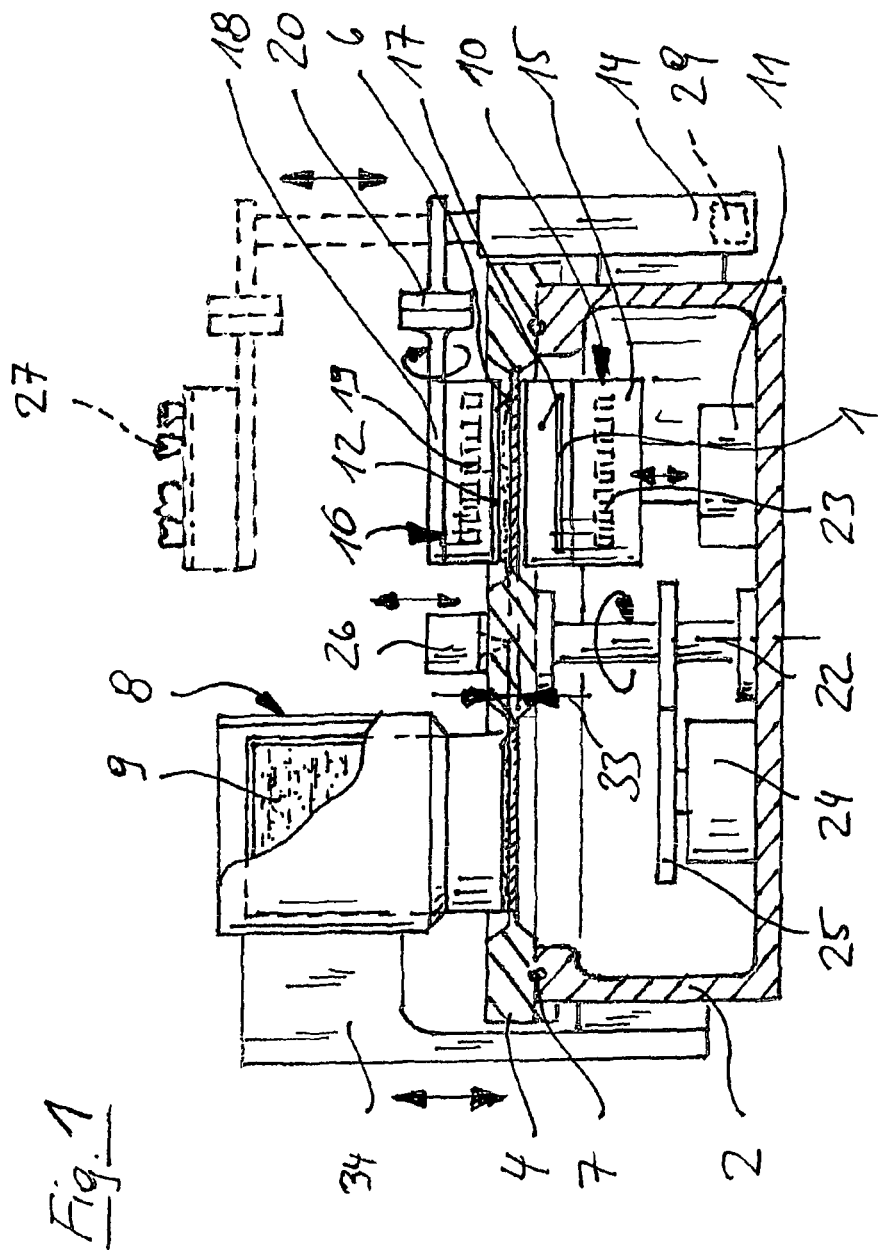
FIG. 1 shows a lateral plan view, partly in section, of a device according to the invention.

The device according to the invention is characterized in that a further exposure unit is provided for exposing the surface area of the build platform from the side opposite from the projecting exposure unit, in that the build platform is formed such that it is at least partially transparent or translucent and in that the control unit is designed to control the further exposure unit, at least while building up the first layer, which adheres to the build platform, for exposure in the prescribed geometry, in order to achieve complete polymerization and adhesive attachment at least of the first layer to the build platform. This is of advantage in particular for light-polymerizable materials in which light is strongly absorbed or diffused, since these materials cannot be polymerized reliably and reproducibly completely by exposure exclusively from the side facing away from the build platform.

Furthermore, this complete polymerization has the effect of producing exact parallelism of the first layer with the vat bottom, which is of great significance for the optimum process of detachment of the further layers.

In a preferred embodiment, the device has at least one vat with an at least partially transparently or translucently formed bottom, into which light-polymerizable material can be filled, the build platform being held in relation to the vat bottom at a settable height above the vat bottom by a lifting mechanism. The control unit is prepared for adapting the relative position of the build platform to the vat bottom by controlling the lifting mechanism after each exposure step for a layer.

In a preferred embodiment, the projecting exposure unit is arranged below the vat bottom for the exposure of the at least partially transparent or translucent vat bottom from below; correspondingly, the further exposure unit is then arranged above the build platform, behind the side thereof that is facing away from the vat bottom, in order to expose the build platform from above.

In the lifting mechanism, and connected to the control unit, there is preferably a force transducer, which is capable of measuring the force exerted by the lifting mechanism on the build platform and sending the measurement result to the control unit, the control unit being prepared for moving the build platform with a prescribed force profile. In particular in the case of ceramic-filled light-polymerizable materials, on account of the high viscosity, great forces may occur when the build platform is moved down into or moved up out of the viscous material, caused by the viscous material being displaced from or sucked in between the build platform and the vat bottom. In order to limit the forces occurring and nevertheless allow the highest possible lowering and raising rates, which speeds up the production process as a whole, the control unit may use the lifting mechanism optimally in a force-controlled manner by force measurement.

Light-emitting diodes are preferably used in the device as the light source of the projecting exposure unit and/or of the further exposure unit. Conventionally, mercury vapor lamps have been used in the case of stereolithography processes with mask projection, which however entails disadvantages since the luminous density of such mercury vapor lamps can vary considerably over time and space, which often makes repeated calibrations necessary. It is therefore preferred to use light-emitting diodes, which show significantly lower variations in intensity over space and time. Nevertheless, in a preferred embodiment, the device is prepared for carrying out a correction or compensation of variations in intensity automatically at prescribed intervals. For this purpose, it may be provided that the exposure unit has a reference sensor, which is formed as a photosensor scanning the entire exposure area or as a CCD camera recording the entire exposure area. The control unit is prepared for operating in a calibration step by exposing the exposure area with a prescribed intensity and using the intensity pattern recorded by the reference sensor for calculating a location-dependent compensation, the application of which produces a uniform intensity in the entire exposure area.

Light-emitting diodes which emit light with different optical wavelengths are preferably used. This makes it possible to process different materials with different photoinitiators in the same device.

The projecting exposure unit and the further exposure unit are preferably designed for the emission of light with an average intensity of 1 mW/cm$^2$ to 2000 mW/cm$^2$, in particular 5 mW/cm$^2$ to 50 mW/cm$^2$.

The projecting exposure unit preferably has a spatial light modulator, in particular a micromirror array controlled by the control unit.

The projecting exposure unit also has at least one reference sensor, which is formed as a photosensor scanning the entire exposure area or as a CCD camera recording the entire exposure area, the control unit being prepared for operating in a calibration step by exposing the exposure area with a control signal that is homogeneous over the entire exposure area and using the intensity pattern recorded by the reference sensor for calculating a compensation mask to achieve a uniform intensity in the entire exposure area. The compensation mask delivers location-dependently in the exposure area a relationship between the signal amplitude controlling the exposure unit and the actual intensity respectively resulting from this. This allows time-dependent or permanently occurring variations of the locational intensity distribution in the exposure area to be compensated, by the projecting exposure unit being controlled by the control unit with a position dependent signal that is inverse to the compensation mask recorded in the last calibration step, so that a uniform actual intensity can be achieved in the exposure area.

In order to achieve a layer thickness of light-polymerizable material over the vat bottom that is as uniform as possible and can be prescribed as exactly as possible, the device according to the invention is preferably constructed as follows. The vat is movable in a horizontal direction with respect to the projecting exposure unit and the build platform. Arranged ahead of the exposure unit and the build platform in the direction of movement of the vat is an application device, for example a doctor blade or a roller, the height of which above the vat bottom can be set. The application device, extending with a lower edge parallel to the vat bottom, smooths the light-polymerizable material to a uniform thickness before it reaches the polymerization region between the exposure unit and the build platform.

To perform this movement between successive exposure steps, the vat may be mounted with its bottom rotatable about a central axis and be turned by a prescribed angle by a drive between successive exposure steps. The projecting exposure unit and the build platform lying above it lie offset radially outward with respect to the central axis, so that in successive exposure steps and rotational movement steps taking place in between the vat bottom is ultimately passed over in the form of a circular ring. The application device, for example a doctor blade or roller or combinations thereof, then lies ahead of the projecting exposure unit in the direction of movement, so that the exposure process takes place after the application device has acted on the layer of material. Multiple doctor blades or rollers or combinations thereof may be provided in order to have a smoothing and rolling effect on the layer. The application device may also be formed in particular by an edge of a discharge channel of the feed device, which lies at a settable height above the vat bottom.

The light-polymerizable material may, for example, be discharged from a feed device, for example a reservoir, into the vat with the partially transparent or translucent bottom, the exposure taking place from below through the transparent or translucent bottom. Between successive exposure steps for the forming of successive layers, the bottom is moved in relation to the exposure unit and the build platform. During the exposure step, the vat is stationary with respect to the exposure unit and the build platform.

By suitable choice of the size of the movement steps of the vat, strategies which allow the vat bottom to be exposed at new places each and every time can be carried out, so that adhesive attachment of the light-polymerizable material to the vat bottom caused by repeated exposure of the same place on the vat bottom can be reduced. In a rotational movement of the vat, for example, the ratio of full circle (360°) to rotational angle increment is preferably not an integral number, in particular also not a rational number. Alternatively, the rotational angle increments may also be varied in a prescribed or random manner, so that the polymerization always takes place in different regions of the vat.

In a preferred embodiment, behind the region of the projecting exposure unit and the build platform there lies a wiper which can be positioned at a prescribable height above the vat bottom and is designed for renewed distribution of the material after the polymerization process. After an exposure step and after the build platform has been raised, a zone without light-polymerizable material, corresponding to the form of the layer last formed, is left behind in the layer of material on the vat bottom. This zone is filled again at the latest when it is passed by the wiper, by renewed distribution of the material on the vat bottom.

The device is preferably designed for the purpose of performing a relative tipping movement between the build platform and the vat bottom when the raising of the build platform is initiated after an exposure step, under the control of the control unit, whereby a more gentle separation of the layer of polymerized material from the vat bottom is achieved, and consequently less stress on the object.

In a preferred embodiment there are a plurality of vats, each of which is assigned a feed device for one of a plurality of light-polymerizable materials, and a drive, which, under the control of the control unit, is capable of moving one of the vats in each case in a selected prescribed sequence between the projecting exposure unit, the further exposure unit and the build platform, this movement being a linear movement in the case where multiple vats are arranged in series or a rotating movement in the case where multiple vats are arranged along a curved path, whereby layers of different materials can be built up in accordance with the selected prescribed sequence.

The feed device preferably has a receptacle for inserting a cartridge with light-polymerizable material, in order to be able in a simple way to use the light-polymerizable material that is desired for the respective building process.

The underside of the build platform is preferably provided with a structuring, for example comprising nubs, channels or grooves, which is provided in or on the lower surface itself and/or in or on a coating or film applied thereto. The at least partially transparent or translucent vat bottom is preferably formed by a film or a sheet containing a polymerization inhibitor. The build platform may, in particular, consist of a high-temperature-resistant material, preferably of zirconium oxide, aluminum oxide, sapphire glass or quartz glass.

A method according to the invention of the aforementioned type is characterized in that, at least during the polymerization of the first layer directly on the build platform, light is irradiated into the side of the build platform opposite from the side with the first layer to be polymerized, the build platform being formed such that it is transparent or translucent in the region of the exposure area in order to achieve complete polymerization and adhesive attachment at least of the first layer on the build platform.

Preferably, the light-polymerizable material on the underside of the build platform is polymerized by exposure from below, the build platform is raised in relation to a vat after each exposure step and light-polymerizable material is newly fed under the layer last formed.

Subsequently, the build platform with the layers formed on it is preferably lowered again into the newly fed light-polymerizable material, so that light-polymerizable material is displaced from the intermediate space, and the distance between the lower surface of the layer last formed and the vat bottom is set in a prescribed manner. In this way, the thickness of the layer to be formed, which corresponds to the distance between the lower surface of the layer last formed and the vat bottom, can be precisely set by mechanically precise setting of the build platform above the vat bottom.

The first layer of light-polymerizable material is preferably polymerized onto a, possibly removable, film or coating arranged on the underside of the build platform.

The displacement of the build platform preferably takes place by raising and/or lowering under force control in accordance with a prescribed force profile, i.e. the force exerted by the lifting mechanism on the build platform is limited with respect to prescribed criteria. As a result, the forces occurring, which may be considerable, particularly in the case of materials of relatively high viscosity, and could detrimentally affect the buildup of the object, can be limited while nevertheless allowing the highest possible lowering and raising rates of the build platform into and out of the light-polymerizable material, which optimizes the speed of the production process as a whole, since it is possible to work at all times with the highest speed at which detrimental effects are still avoided.

Light-polymerizable material is preferably discharged from a feed device into a vat with an at least partially transparent or translucent bottom, the exposure taking place from below through the vat bottom of an at least partially transparent or translucent form, the bottom of the vat being moved in relation to the projecting exposure unit and the further exposure unit and the build platform between successive exposures for the forming of successive layers, there being arranged ahead of the exposure units and the build platform in the direction of movement an application device, preferably a doctor blade or a roller, the height of which above the vat bottom is set in order to bring the light-polymerizable material to a uniform layer thickness.

The vat is preferably rotatably mounted and is turned by a prescribed angle about the axis of rotation between successive layer building steps.

Alternatively or in addition, the vat may be mounted such that it can be moved laterally and may be moved over a prescribed distance in the horizontal direction between successive layer building steps.

To allow the build up of objects using different materials, a plurality of different materials can be used for building up layers in a selectable sequence in successive layer building steps, by a plurality of vats, each assigned a feed device with one of the plurality of materials, being moved in a selected sequence between the projecting exposure units and the build platform, this movement being a linear movement in the case where multiple vats are arranged in series or a rotating movement in the case where multiple vats are arranged along a curved path.

In a preferred embodiment, a particle-filled, for example ceramic-filled, light-polymerizable material is used for the production of the object and the organic constituents are burned out from the finished object before the object is sintered. The particle fraction of the light-polymerizable material may preferably consist of an oxide ceramic or a glass ceramic.

The light-polymerizable material on the underside of the build platform is preferably polymerized by exposure from below, after which the build platform is raised in relation to a vat for the light-polymerizable material after each exposure step and light-polymerizable material is newly fed under the layer last formed. In this case, the first layer of light-polymerizable material may be polymerized onto a removable film or coating arranged on the underside of the build platform.

The object to be produced by the method according to the invention may be, for example, a green blank for a dental restoration, in which case the light-polymerizable material may be, for example, a ceramic-filled photopolymer. The build platform preferably has a sheet of a high-temperature-resistant material, preferably of zirconium oxide, aluminum oxide, sapphire glass or quartz glass. A transparent polymer film may be adhesively attached on such a ceramic base in order to form the build platform, it being possible for the polymer film to be provided with structurings such as nubs, channels or the like on the side that comes into contact with the photopolymer, in order to achieve still better adhesive attachment of the ceramic-filled photopolymer. After the successive buildup of the green blank, the build platform with the green blank adhesively attached thereto can be removed and introduced directly into the sintering furnace. During the debinding of the component, not only the organic resin component but also the polymer film of the build platform decomposes, and after the sintering the sintered ceramic object consequently lies loosely on the sheet of the build platform and can be removed.

In the case of the method according to the invention, a plastic may preferably be used for producing the object, the object being embedded in an embedding compound after it has been produced and burned out after the embedding compound has solidified, and a different material, in particular a dental ceramic material or metal or an alloy, being forced into the cavities created in the embedding compound.

In the case of a preferred method, a dental composite may be used for the production of the object and, after it has been produced, the object may be heat-treated and subsequently polished or coated and subsequently heat-treated.

In the case of a method according to the invention, the ceramic fraction of the ceramic-filled photopolymer preferably consists of an oxide ceramic or a glass ceramic, in particular zirconium oxide, aluminum oxide, lithium disilicate, leucite glass ceramic, apatite glass ceramic or mixtures thereof.

In the case of a method according to the invention, after carrying out an exposure step with the vat stationary, the build platform is preferably raised in order to lift off the layer formed from the vat bottom. For this purpose, a slight relative tipping movement between the build platform and the vat bottom is preferably carried out, since, after the polymerization, adhesive attachment of the layer formed to the vat bottom could lead to excessive mechanical stress on the layer just formed or the entire component if it were pulled vertically upward. After the build platform has been raised, a zone without light-polymerizable material, corresponding to the form of the layer last formed, is left behind in the layer of material on the vat bottom. This zone is filled again at the latest when it is passed by the doctor blade or the roller or by an optional additional wiper, by renewed distribution of the material on the vat bottom.

The following exemplary embodiment relates to the production of a green blank for a dental restoration.

Firstly, the main components of the device are described with reference to FIGS. 1 and 2.

Figure 2:
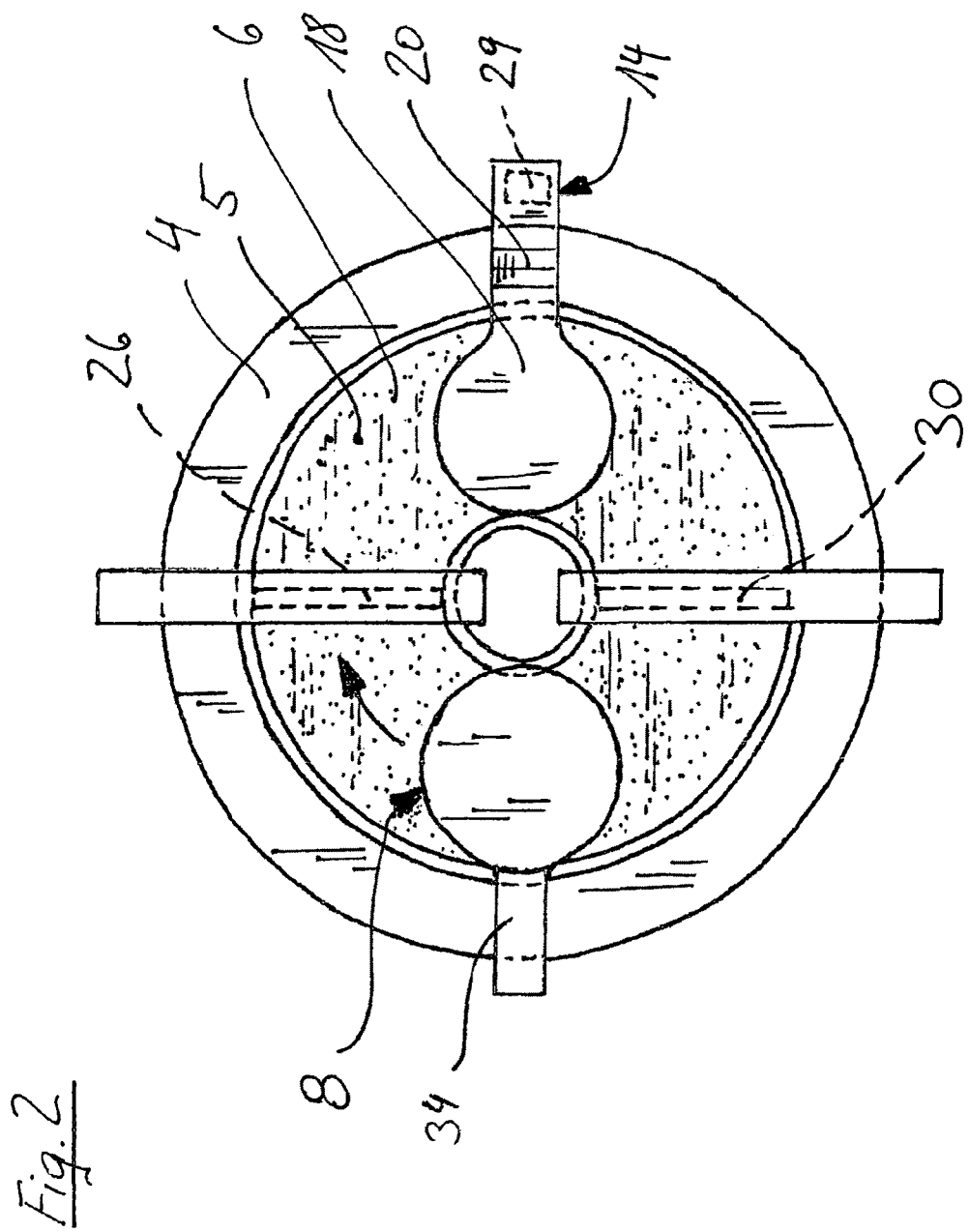
FIG. 2 shows a plan view of the device from FIG. 1, from above.

In the embodiment represented in FIGS. 1 and 2, the device has a housing 2, which serves for accommodating and fitting the other components of the device. The upper side of the housing 2 is covered by a vat 4, which has, at least in the regions intended for exposures, a transparent and planar vat bottom.

Provided in the housing 2, under the vat bottom 4, is a projecting exposure unit 10, which can, under the control of a control unit 11, expose a prescribed exposure area on the underside of the vat bottom 6 selectively with a pattern in the desired geometry.

The projecting exposure unit 10 preferably has a light source 15 with multiple light-emitting diodes 23, a luminous power of approximately 15 to 20 mW/cm2 preferably being achieved in the exposure area. The wavelength of the light radiated from the exposure unit preferably lies in the range from 400 to 500 nm. The light of the light source 15 is modulated location-selectively in its intensity by way of a light modulator 17 and imaged in the resultant intensity pattern with the desired geometry on the exposure area on the underside of the vat bottom 6. Various types of so-called DLP chips (digital light processing chips) may serve as light modulators, such as for example micromirror arrays, LCD arrays and the like. Alternatively, a laser may be used as the light source, the light beam of which successively scans the exposure area by way of a movable mirror, which may be controlled by the control unit.

Provided over the projecting exposure unit 10 on the other side of the vat bottom 6 is a build platform 12, which is held by a lifting mechanism 14 with a carrier arm 18, so that it can be held over the vat bottom 6 above the exposure unit 10 in a height-adjustable manner. The build platform 12 is likewise transparent or translucent.

Arranged above the build platform 12 is a further exposure unit 16, which is likewise controlled by the control unit 11 in order, at least during the forming of the first layer under the build platform 12, also to irradiate light from above through the build platform 12, in order thereby to achieve dependable and reliably reproducible polymerization and adhesive attachment of the first polymerized layer on the build platform.

Also provided above the surface of the vat 4 is a feed device 8 with a reservoir in the form of an exchangeable cartridge 9 filled with light-polymerizable material. Under the control of the control unit 11, ceramic-filled light-polymerizable material can be successively discharged from the feed device 8 onto the vat bottom 6. The feed device is held by a height-adjustable carrier 34.

The vat 4 is mounted rotatably about a vertical axis 22 on the housing 2 by a bearing 7. A drive 24, which, under the control of the control unit 11, sets the vat 4 in a desired rotational position, is provided.

A wiper 30, which can undertake various functions, as explained further below, may be arranged between the exposure unit 12 and the feed device 8 in the direction of rotation, at a suitable height above the vat bottom 6.

As can be seen from FIG. 2, lying between the feed device 8 and the exposure unit 12, above the vat bottom 6, is an application device 26, here in the form of a doctor blade 26, which can be positioned at a suitable height above the vat bottom 6, in order in this way to smooth material that has been discharged from the feed device 8 onto the vat bottom 6 before it reaches the exposure unit 12, in order thereby to ensure a uniform and prescribed layer thickness. Alternatively or in addition to the doctor blade, one or more rollers or further doctor blades may belong to the application device, in order to act in a smoothing manner on the layer of material.

The pivot arm 18 carrying the build platform 12 is connected by way of a pivot joint 20 to the vertically displaceable part of the lifting mechanism 14. Also provided in the lifting mechanism 14 is a force transducer 29, which measures the force exerted by the lifting mechanism 14 on the build platform 12 during the lowering and raising thereof and sends the measurement result to the control unit 12. As described further below, said control unit is designed for the purpose of controlling the lifting mechanism 14 on the basis of a prescribed force profile, for example to limit the force exerted on the build platform 12 to a maximum value.

The way in which the device represented in FIGS. 1 and 2 functions can be summarized as follows. Under the control of the control unit, a prescribed amount of ceramic-filled light-polymerizable material 5 is discharged from the feed device 8 onto the vat bottom 6. By controlling the drive 24, the control unit 11 instigates a turning of the vat bottom 6 about the axis of rotation 22, so that the discharged material passes the application device 26, here a doctor blade, which smooths the light-polymerizable material to a prescribed layer thickness 32, which is determined by the height setting of the application device 26. Furthermore, by turning of the vat 4, the material is brought into the region between the build platform 12 and the exposure unit 10.

After stopping the turning movement of the vat 4, here there then follows the lowering of the build platform 12 into the layer of light-polymerizable material 5 formed on the vat bottom 6, which is explained below on the basis of FIGS. 3 to 5. In the state shown in FIG. 3, a layer of light-polymerizable material 5 with a prescribed thickness 32 is formed on the vat bottom, the build platform 12 still being located above the layer 5 in this state. Attached to the underside of the build platform 12 is a film 13, which will be discussed further below. From the state represented in FIG. 3, a lowering of the build platform 12 then takes place by the lifting mechanism 14 under the control of the control unit 11, so that the build platform 12 with the film 13 on the underside is immersed into the layer of light-polymerizable material 5 and, as it is lowered further, displaces said layer partially out of the intermediate space between the film 13 and the upper surface of the vat bottom 6. Under the control of the control unit 11, the build platform 12 is lowered by the lifting mechanism 14 to the vat bottom in such a way that a layer with a precisely prescribed layer thickness 21 is defined between the build platform and the vat bottom. As a result, the layer thickness 21 of the material to be polymerized can be precisely controlled.

During the immersion of the build platform 12 into the light-polymerizable material 5 and the further lowering into the position shown in FIG. 4, great forces could occur, particularly when material of relatively high viscosity is displaced, if the lowering of the build platform were to take place at the prescribed rate. In order to prevent the layers of material that build up during the lowering of the build platform 12 into the light-polymerizable material 5 from being exposed to great forces, in the lifting mechanism there is the aforementioned force transducer 29, which measures the force exerted on the build platform 12 and sends the measurement signal to the control unit 11. This control unit is only prepared for controlling the lifting mechanism in such a way that the force recorded by the force transducer 29 follows prescribed criteria, in particular that the force exerted does not exceed a prescribed maximum force. As a result, on the one hand the lowering of the build platform 12 into the light-polymerizable material 5 and the raising of the build platform out of said material can be carried out in a controlled manner such that the forces exerted on the build platform, and consequently also on the layers already formed, are limited and, as a result, detrimental effects are avoided during the buildup of the object, and on the other hand the lowering and raising of the build platform 12 can be carried out at the maximum possible rate at which detrimental effects on the object to be built up are still just avoided, in order in this way to achieve an optimal process rate.

After the lowering of the build platform into the light-polymerizable material 5, into the position shown in FIG. 4, there then follows the first exposure step for the polymerization of the first layer 28 on the build platform 12, the invention providing that the further exposure unit 16 is thereby also actuated (at the same time or with a time delay), in order to ensure reliable adhesive attachment of the first polymerization layer 28 to the build platform. During the exposure process, the vat 4 is kept stationary, i.e. the drive 24 remains switched off. After the exposure of one layer, the build platform 12 is raised by the lifting mechanism 14. In this case, however, before the raising of the build platform 12, a relative tipping movement between the build platform 12 and the vat bottom 6 is preferably carried out first. This slight tipping movement is intended to serve the purpose of detaching the last-polymerized layer of the object 27 from the vat bottom 6 with less mechanical stress. After this tipping movement and detachment of the layer last formed, the build platform is raised by a prescribed amount, as shown in FIG. 5, so that the layer last formed lies above the light-polymerizable material 5 on the object 27.

Subsequently, material is again discharged from the feed device 8 and the vat 4 is turned by a prescribed rotational angle by the drive 24, the material that moves past the doctor blade again being brought to a uniform layer thickness. This series of steps, with the forming of successive layers of a prescribed form of contour, is continued until the succession of layers with respectively prescribed geometry provides the desired form of the ceramic green blank.

The wiper 30, provided behind the exposure unit and above the vat bottom 6, may have various functions. For example, when it has been lowered fully onto the vat bottom 6, it may serve the purpose of collecting the material from the vat bottom and carrying it away or returning it into the feed device 8, which should take place at the end of a building process. During a building process, when it is raised slightly with respect to the vat bottom 6, the wiper 30 serves the purpose of distributing the material again, in particular pushing the material back into the "holes" that have been created in the layer of material by the exposure process after raising of the build platform 12.

After the completion of a building process, the build platform 12 with the exposure unit 16 fitted above it, can be pivoted upward as a whole by pivoting the pivot arm 18 about the joint 20, as indicated by dashed lines in FIG. 1. After that, there is better access to the vat 4, for example to allow the latter to be cleaned or exchanged.

After the described buildup of the green blank from polymerized ceramic-filled material, said blank must be removed from the device and fed to a firing furnace, in which a decomposition of the polymerized binder (debinding) is brought about by the thermal treatment and a sintering of the ceramic material is carried out. To simplify the handling of the built-up body, the build platform is designed such that it can be easily detached from the carrier arm 18. Then the build platform, with the built-up ceramic-filled object 27 adhesively attached to it, can be removed from its carrier 18 and placed in a firing furnace. In order to allow this preferred simple removal of the built-up dental restoration element of ceramic-filled polymer, the build platform must however be produced from a high-temperature-resistant material, for which zirconium oxide, aluminum oxide, sapphire glass or quartz glass may serve for example. Possible as an alternative to this is a self-adhesive, transparent film, which may be structured with nubs, channels, scores etc. on the side facing the photopolymer, for better adhesive attachment, and can be removed after the building process by simple detachment from the build platform or together with the build platform and passed together with the film into the firing furnace for debinding/sintering.

Figure 7:
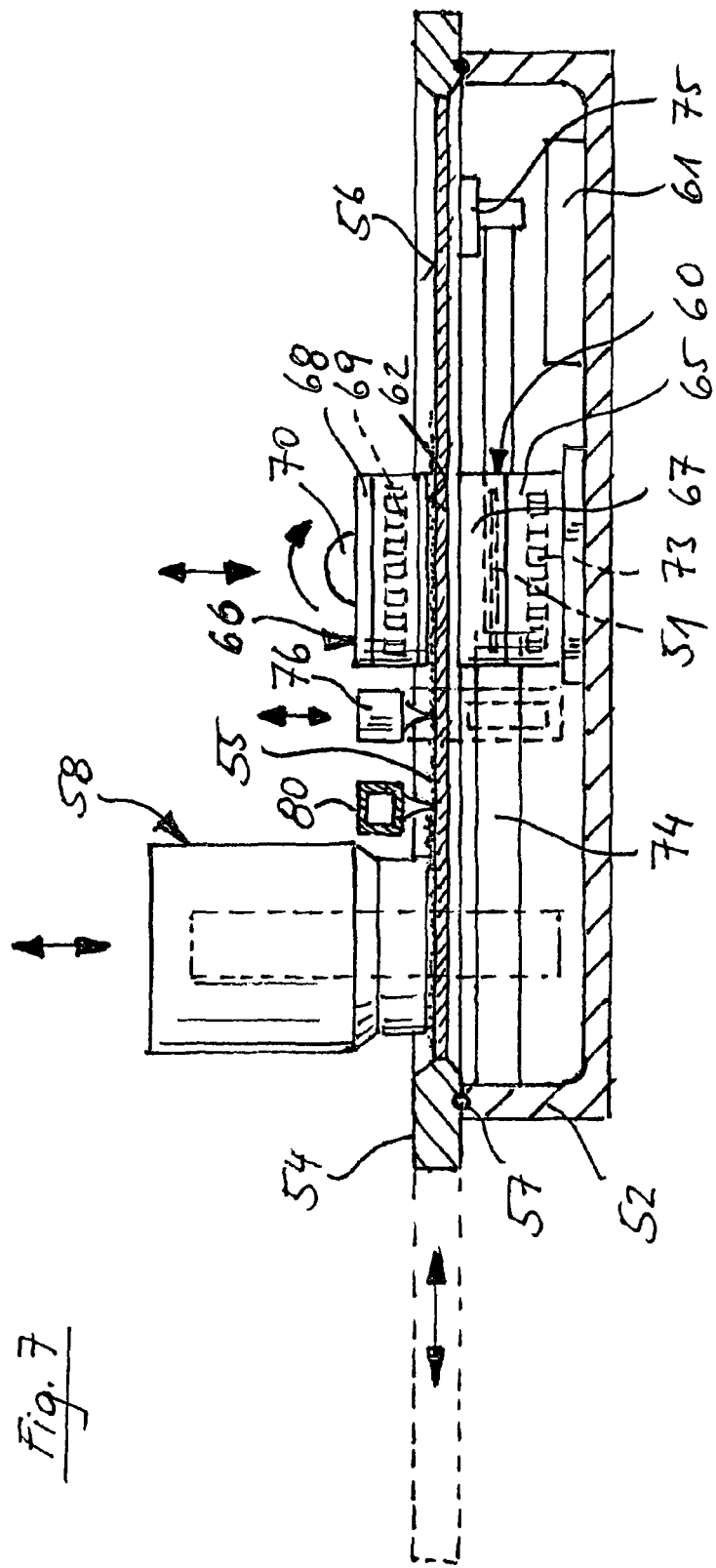
FIG. 7 shows a lateral plan view, partly in section, of the device of the second embodiment from FIG. 6.

As compared with the device from FIGS. 1 and 2 with a rotatable vat, FIGS. 6 and 7 show an alternative embodiment, in which the vat 54 is designed such that it is movable linearly back and forth. In this embodiment, a vat 54 is mounted linearly movably on the housing 52 in a bearing 57. Above the vat 54, the feed device 58 is arranged in a height-adjustable manner. Offset from the feed device 54 with respect to the linear direction of movement, the build platform 62 is held above the vat 54 on a pivot arm 68, which belongs to a lifting mechanism 64. The pivot arm 68 is in turn provided with a pivot joint 70, which allows the pivot arm 68, after being raised in the vertical direction, to be turned by 180°, after which the build platform 62 with the object built up on it faces upward, and in this position can be easily handled.

Located below the build platform 62 and the vat bottom 56 is the projecting exposure unit 60, in which a light source 65 with light-emitting diodes 73 is arranged. The light of the light source 65 is projected by way of a light modulator 67 and through the transparent vat bottom 56 onto the build platform 62. Also present in the projecting exposure unit 60 is a reference sensor 51, which is used in a calibration step for the purpose of recording the actual intensity distribution in the exposure area when the light modulator is controlled in such a way as to obviate any locational dependence or modulation over the exposure area. From the deviation of the intensity distribution actually recorded, a control profile (compensation mask) for the light modulator can then be calculated by inversion and provide an intensity that is actually uniform over the exposure area. A corresponding reference sensor 1 is also present in the case of the embodiment from FIGS. 1 and 2.

Arranged in the direction of movement of the vat 54 (indicated by the double-headed arrow in FIGS. 6 and 7) are an application device 76, which is held in a height-adjustable manner above the vat bottom 56 and here is in the form of a doctor blade, the lower edge of which lies at a suitable distance from the surface of the vat bottom, and a wiper 80.

The way in which the device shown in FIGS. 6 and 7 functions corresponds to the method steps described above with reference to FIGS. 3 to 5, apart from the difference of the linear movement back and forth of the vat 54 instead of the rotating movement of the vat 4. Firstly, instigated by the control unit 61, which actuates the drive 75, the vat 54 is displaced from the position shown in FIG. 7 to the left into the position shown by dashed lines. In this case, light-polymerizable material is discharged by the feed device 58 onto the vat bottom 56, the amount and variation over time of the discharge likewise being prescribed by the control unit 61. After that, by reversing the drive 75, the control unit 61 causes the vat 54 to be displaced back again. As this happens, the light-polymerizable material 55 discharged onto the vat bottom 56 first passes the wiper 80 and then the application device 76, which ensure a uniform distribution and uniform layer thickness of the light-polymerizable material 55, before it reaches the intermediate space between the build platform 62 and the projecting exposure unit 60. After that, the drive 75 is stopped, whereupon the series of steps as described above in conjunction with FIGS. 3 to 5 is executed, the build platform 62 being immersed into the layer of light-polymerizable material 55 and a layer with prescribed thickness being defined between the build platform and the vat bottom by setting of the distance from the vat bottom. After that, the actuation of the projecting exposure unit 60 takes place to generate an exposure pattern with prescribed geometry, the further exposure unit 66 with its light-emitting diodes 69 also being actuated in this connection, at least during the generation of the first layer directly on the build platform 62, in order to achieve complete polymerization and reliable adhesive attachment of the first layer to the build platform 62.

After polymerization of the first layer with the desired geometry, the build platform 62 is raised again by actuating the lifting mechanism 64, so that the polymerized layer formed is raised above the level of the light-polymerizable material 55.

After that, the series of steps described is repeated, i.e. the vat 54 is again displaced to the left, light-polymerizable material is discharged from the feed device 58 and this material is distributed uniformly by the wiper 80 and the application device 76 when the vat 54 is pushed back to the right, after which, by switching off the drive 75, the lifting mechanism 64 lowers the build platform again, so that the last-formed polymerized layer is immersed into the light-polymerizable material 55 and is brought to a prescribed distance above the vat bottom, in order to polymerize the layer of material that is then lying in the intermediate space in the next exposure step. The increment of the movement back and forth can of course be varied again, in order to avoid polymerization always being carried out over the same place on the vat bottom.

The lifting mechanism 64 is in turn provided with a force transducer 79, the measured values of which are used by the control unit 61 in the way described above in connection with the first embodiment for limiting the force that is exerted on the build platform during the lowering and raising of the build platform.

Methods in which multiple different ceramic-filled photopolymerizable materials are used for building up the green blank may preferably also be used. This may take place, for example, by a plurality of vats being provided, each with an assigned reservoir with different materials. These vats may then be moved to the exposure unit and the build platform in the manner of a changeover carrier, in order to process different materials in a prescribed sequence. For this purpose, the multiple vats may, for example, be arranged in series one behind the other on a carrier, which is then linearly movable with respect to the exposure unit and the build platform, in order to provide a desired vat in each case. Alternatively, a plurality of rotatable vats, one of which is represented in FIGS. 1 and 2, may be arranged on a circular ring of a larger plate, which for its part is in turn rotatable, in order in each case, by setting the rotational position of the plate, to bring a desired vat into the position between the exposure unit and the build platform in which the polymerization step of the respective layer is then carried out.

Figure 8:
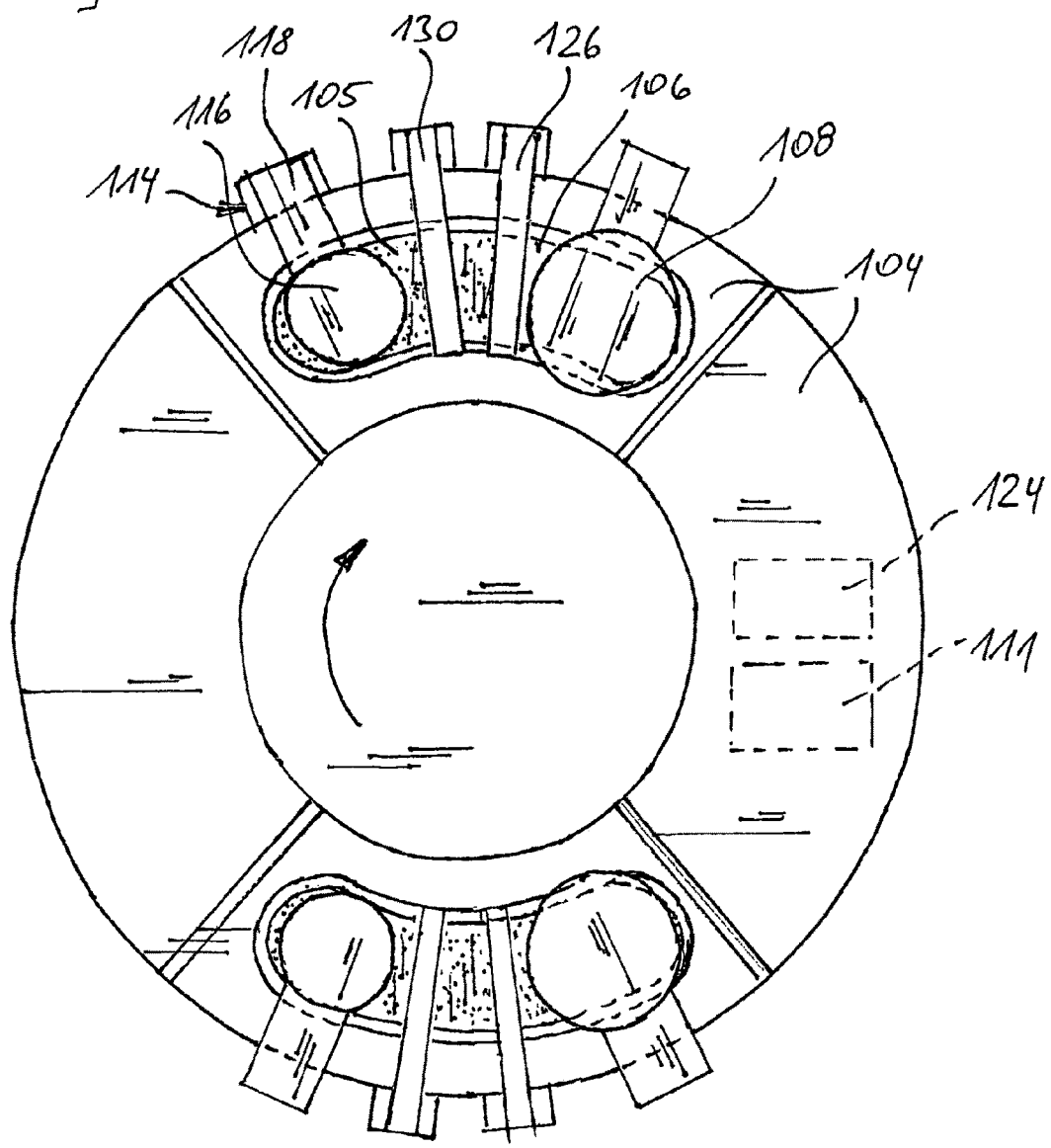
FIG. 8 shows a plan view from above of a third embodiment of the device.

A special embodiment of a device with which various light-polymerizable materials can be used for building up an object is shown in FIG. 8 in a schematic plan view from above. Here there are four vats 104 on a turntable, arranged in the form of a circular ring. The arrangement of the feed device 108, the further exposure unit 116 on a lifting mechanism 114 as well as the wiper 130 and the application device 126 lying in between is largely similar to the arrangement of the device from FIGS. 6 and 7, with the exception of the fact that the components are not arranged along a linear path and the vat is not linearly movable, but instead the components are arranged along a segment of a circular ring and the vat correspondingly has the form of a segment of a circular ring. Between successive exposure steps in the same vat 104, the vat is moved back and forth by an angle of approximately less than 90°, so that in turn a movement back and forth is obtained between the feed device 118 and the build platform located under the further exposure unit 108.

If at a specific point in time one of the materials from one of the three other vats 104 is to be used, the turntable is turned by an angle corresponding to 90°, 180° or 270°, in order to bring one of the following vats to the device under consideration for building up the object.

As indicated at the bottom in FIG. 8, a further device for building up objects, which can operate in parallel with the device shown at the top, may be provided on the turntable in the region of another segment of a circular ring.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. A device for processing light-polymerizable material for building up an object in layers, using lithography-based generative fabrication, comprising
    a build platform for building up the object,
    a projecting exposure unit, which can be controlled for position selective exposure of a surface on the build platform with an intensity pattern with prescribed form, and
    a control unit, which is arranged to polymerize in successive exposure steps layers lying one above the other on the build platform, respectively with prescribed geometry, by controlling the projecting exposure unit, in order in this way to build up the object successively in the desired form, which results from the sequence of the layer geometries, and
    a further exposure unit for exposing the surface area of the build platform from the side opposite from the projecting exposure unit, the build platform being formed such that it is at least partially transparent or translucent and the control unit being designed to control the further exposure unit, at least while building up the first layer, which adheres to the build platform, for exposure in the prescribed geometry, wherein the further exposure unit comprises light-emitting diodes, the further exposure unit arranged above the build platform,
    at least one vat with an at least partially transparently or translucently formed bottom, into which light-polymerizable material can be filled, wherein the build platform is held by a lifting mechanism above the vat bottom, so that its height in relation to the vat bottom, which is stationary in height during use, can be set, and wherein the control unit is arranged to adapting the relative position of the build platform to the vat bottom by controlling the lifting mechanism after each exposure step for a layer, and is arranged to lower, after renewed feeding of light-polymerizable material, the build platform with the layers formed on it, if any are present, again into the newly fed light-polymerizable material, so that light-polymerizable material is displaced from the remaining intermediate space with respect to the vat bottom, and the distance between the lowered lower surface of the build platform or of the layer last formed on it and the vat bottom is set in a prescribed manner to define a layer of light-polymerizable material to be polymerized in the next exposure step, the layer having a defined layer thickness equal to the set distance.

2. The device as claimed in claim 1, wherein the projecting exposure unit is arranged below the vat bottom for exposure through the at least partially transparent or translucent vat bottom from below and in that the further exposure unit is arranged for exposure through the at least partially transparent or translucent build platform from above.

3. The device as claimed in claim 2, wherein, in the lifting mechanism, and connected to the control unit, there is a force transducer, which is capable of measuring the force exerted by the lifting mechanism on the build platform and sending the measurement result to the control unit, the control unit being arranged to move the build platform with a prescribed force profile.

4. The device as claimed in claim 1, wherein light-emitting diodes serve as a light source of the projecting exposure unit and/or of the further exposure unit.

5. The device as claimed in claim 4, wherein the light-emitting diodes are designed for emitting light with different optical wavelengths.

6. The device as claimed in claim 1, wherein the projecting exposure unit and the further exposure unit emit light with an average intensity of 1 mW/cm$^2$ to 2000 mW/cm$^2$, in particular 5 mW/cm$^2$ to 50 mW/cm$^2$.

7. The device as claimed in claim 1, wherein the projecting exposure unit has a spatial light modulator controlled by the control unit.

8. The device as claimed in claim 1, wherein the projecting exposure unit also has at least one reference sensor, which is formed as a photosensor scanning the entire exposure area or as a CCD camera recording the entire exposure area, the control unit being arranged to perform in a calibration step an exposure by exposing the exposure area with a control signal that is homogeneous over the entire exposure area and using the intensity pattern recorded by the reference sensor for calculating a compensation mask to achieve a uniform intensity in the entire exposure area.

9. The device as claimed in claim 1, wherein the vat is movable in a horizontal direction with respect to the projecting exposure unit and the build platform and in that arranged ahead of the exposure unit and the build platform in the direction of movement is an application device, the height of which above the vat bottom can be set.

10. The device as claimed in claim 9, wherein the vat is mounted rotatably about a central axis of rotation, the projecting exposure unit lying below the vat bottom and the build platform lying above it, offset in the radial direction with respect to the central axis, in that a drive is provided and, under the control of the control unit, is capable of turning the vat by a prescribed angle about the central axis of rotation between successive exposure steps, a feed device for discharging light-polymerizable material into the vat, the application device and the combination of the exposure unit and the build platform are located following one another in the direction of movement.

11. The device as claimed in claim 10, wherein, behind the region of the projecting exposure unit and the build platform in the direction of rotation there lies a wiper, which can be positioned at a prescribable height above the vat bottom and is designed for renewed distribution of the material after the polymerization process.

12. The device as claimed in claim 1, comprising a plurality of vats, each of which is assigned a feed device for one of a plurality of light-polymerizable materials, and a drive, which, under the control of the control unit, is capable of moving one of the vats in each case in a selected prescribed sequence between the projecting exposure unit, the further exposure unit and the build platform, this movement being a linear movement in the case where multiple vats are arranged in series or a rotating movement in the case where multiple vats are arranged along a curved path.

13. The device as claimed in claim 1, wherein the feed device has a receptacle for inserting a cartridge with light-polymerizable material.

14. The device as claimed in claim 1, wherein lithography-based generative fabrication comprises rapid prototyping.

15. The device as claimed in claim 7, wherein the spatial light modulator comprises a micromirror array.

16. The device as claimed in claim 7, wherein the micromirror array comprises a DLP—Digital Light Processor.

17. The device as claimed in claim 9, wherein the application device comprises a doctor blade or a roller.

18. The device as claimed in claim 4, wherein the light-emitting diodes of the further exposure unit are fixed directly on the upper surface of the build platform.

* * * * *